United States Patent [19]
Chen et al.

[11] Patent Number: 6,129,919
[45] Date of Patent: Oct. 10, 2000

[54] METHOD OF PRODUCING FERMENTED SWORD BEANS

[75] Inventors: Chien Chen, Yi Lan Hsien; Fung-Jou Lu, Taipei; Yun-Lai Chan, Taichung Hsien; Tzong-Hann Lin, Taipei, all of Taiwan

[73] Assignee: Alfa Biotechnology Co., Ltd., Yi Lan Hsien, Taiwan

[21] Appl. No.: 09/325,718

[22] Filed: Jun. 4, 1999

[51] Int. Cl.⁷ ..................................................... A01N 65/00
[52] U.S. Cl. .......................................... 424/195.1; 435/41
[58] Field of Search ............................. 435/41; 424/195.1

[56] References Cited

U.S. PATENT DOCUMENTS 6,004,558  12/1999  Thurn et al. .......................... 424/195.1

OTHER PUBLICATIONS

Computer Abstract BIOSIS 1984:349509 Jokl et al "Nutritive Values of Leaf Protein Concentrates From Tropical Legumes and From Leaves of Forest Trees" NTUR Rep INT (1984) 30 (1) 87–94.

Computer Abstract Caplus 1987:99542 Ozaki "Plant Regeneration From Hyupocotyl and Shoot Meristem Culture of Sword Bean (Canavalia Gladiata)" Shokubusu Soshiki Baiyo (1986) 3(2) 78–82.

*Primary Examiner*—Herbert J. Lilling
*Attorney, Agent, or Firm*—Rosenberg, Klein & Lee

[57] ABSTRACT

A method of producing fermented sword beans to obtain composition of the sword bean that has inhibition action on cancer cells. The method includes steps of selecting proper sword beans and soaking the sword beans in an adequate amount of water, disinfecting the sword beans under high pressure and high temperature of 105° C. for one hour, letting the sword beans cool to 38° C., well mixing the sword beans with *Aspergillus oryzae* of 1.5/1000% in concentration, allowing the mixture to ferment in three separated stages for total 80 hours, adding water of five times in volume of the fermented mixture and well mixing them, extracting to obtain clear solution of the fermented sword beans, and freeze-drying the solution into powder. Tests conducted in laboratory indicate that liver cancer cells, HepG2, have a viability dropped by 80% when treated with the fermented sword bean solution of 200 µg/ml in concentration, and zero when treated with the same solution of 400 µg/ml in concentration, while the viability of normal liver cell line, Chang, is only affected by about 10%.

4 Claims, 2 Drawing Sheets

METHOD OF PRODUCING FERMENTED SWORD BEANS

BACKGROUND OF THE INVENTION

The present invention relates to a method of producing fermented sword beans, and more particularly to a quick and economical method for preparing fermented sword bean solution.

India is the origin of the sword bean. However, the sword bean is also grown in Taiwan and some areas in China. In Taiwan, the sword bean was rarely taken as food. People usually use its creeping tendrils to decorate fences. According to some literatures, except being served as daily dish among a very small number of Taiwanese indigenes who fry green pods of sword beans and shredded meat together, the sword bean is rarely used as food. There are also records that some people in Taiwan use the seeds, the skin of seeds, and the roots of the sword bean plant as medicine for improving circulation, reducing inflammation, killing pain, etc. Being involved in Pacific War during World War II, people in Taiwan encountered serious shortage of food and many edible wild plants were taken as food at that time. Records indicate that mashed sword bean and sword bean jelly had been one of the common foods at that time.

The scientific name of sword bean is *Canavalia gladiata* (Jacq.) DC. There is another type of sword bean that is also classified as a herbaceous plant and has the scientific name of *Canavalia ensiformis* (L.) DC. The seeds of these two types of sword bean have extremely close appearance and are pharmacologically similar to one another. The sword bean contains urea enzyme, blood cell agglutinin, canavanine, starch, protein, fat, etc. The green bean of sword bean contains *Canavalia glibberellin* I & II. The other type of sword bean, that is, the *Canavalia ensiformis* (L.) DC, is important for many types of globulin it contains, including the most important Concanavalin A.

In a report entitled "The Transformed Cells: Unlocking the Mysteries of Cancer" made by Steven A. Rosenberg, it is indicated that lymph cells around cancer tissue will have memory ability, and therefore, when they meet the cancer tissue, the lymph cells will easily access and destroy the cancer tissue to suppress the growth and development of the cancer tissue and even reduce the size of tumor, and that proper amount of Lectin can speed up the division of killer cells. There are British scholars suggesting hypodermic injection of Lectin and it is found such injection has pretty good effect on suppressing tumor cells. However, the injection area tends to inflame, and continuous injection will cause swelling and even ulcer on the skin that is uneasy to heal.

In 1987, another scholar found from laboratory experiments that Lectin orally taken into human body will not be completely decomposed into amino acid. To the contrary, most part of the orally taken Lectin quickly reaches the digestive tract and combines with lymph cells. This is the exact mechanism making the Lectin effective. The sword bean is rich in Con A that is a type of Lectin and has special effect on cancer prevention. Lectin is one kind of protein and will lose its effectiveness in anti-cancer when it is heated. Therefore, it is stressed in prior study that the sword bean is pharmacologically useful only when it is orally taken before being cooked. A conventional method of preparing the sword bean for medical use includes the steps of grinding the sword beans and extracting juice from the ground sword beans, purifying the extracted juice of sword beans through a series of processes to extract Con A from the juice, and making troches from the extracted Con A. The extraction must be proceeded completely at a temperature below 0° C., or the purified Con A will lose its activity.

SUMMARY OF THE INVENTION

In view that sword beans can be conveniently obtained in Taiwan, it is therefore a primary object of the present invention to provide a new method for extracting medically useful composition from the sword beans at normal temperature, so as to eliminate many limitations in the conventional method for preparing troches of extracted Con A from sword beans for oral administration. Many studies and experiments have been conducted by the inventor since 1997 in an attempt to develop a quick and non-expensive method for preparing fermented sword bean solution. The method mainly includes the steps of disinfecting the sword beans under high pressure and high temperature, cooling the disinfected sword beans to a predetermined temperature and adding *Aspergillus oryzae* having a concentration of 1.5/1000% into the disinfected and cooled sword beans, letting the sword beans ferment for 80 hours in three separated stages, and adding water of five times in volume of the mixture of sword beans and *Aspergillus oryzae* and well mixing the fermented sword beans with the water to obtain even solution thereof, and freeze-drying the obtained fermented sword bean solution into powder for use. It has been found from many experiments that the fermented sword bean solution obtained from the above-described steps indeed has inhibition action on tumor cells and completely removes human liver cancer cell line, HepG2. And it is also found that only less than 10% of normal human liver cell line (Chang) would be affected by the fermented sword bean solution. Such a result is acceptable and meets the inventor's satisfaction from a medical viewpoint. Moreover, the preparation of such fermented sword bean solution is time and cost saving compared to the conventional method of preparing Con A-contained troches from raw sword beans.

BRIEF DESCRIPTION OF THE DRAWINGS

The method and the effect of the product thereof may be best understood by referring to the following detailed description of the preferred embodiment and the accompanying drawings, wherein.

DETAILED DESCRIPTION OF THE PREFERRED EMBODIMENTS

In the method of the present invention for producing fermented sword bean solution includes following steps:
1. Soaking selected and screened sword beans in adequate amount of water;
2. Disinfecting the sword beans soaked in the water under a high pressure and a high temperature of 105° C. for one hour;
3. Waiting until the temperature lowers to 38° C.;
4. Adding *Aspergillus oryzae* having a concentration of 1.5/1000% into the disinfected and cooled sword beans and fully stirring the mixture before dispensing the mixture into culture well plates;
5. Letting the mixture obtained from step 4 ferment in three separated stages:

In the first stage: culturing the mixture at a temperature of 35° C. and a relative humidity between 95% and 100% for 24 hours;

In the second stage: continuing the culture of the mixture at a temperature between 35° C. and 38° C. and a relative humidity between 85% and 90% for another 24 hours; and In the third stage: continuing the culture of the mixture at a temperature between 30° C. and 33° C. and a relative humidity between 70% and 80% for another 32 hours;

6. After the fermentation process in step 5, adding water of five times in volume of the fermented mixture into each well plate and well mixing the fermented sword beans with the water;

7. Extracting and separating the mixture obtained in step 6 to obtain clear solution; and 8. Freeze-drying the solution obtained in step 7 to produce dried powder of fermented sword beans.

The pharmacological effect of the powdered fermented sword beans produced in the above-described method is tested and proven effective in suppressing cancer cells through following experiment:

a. The cells adopted for test in the experiment include:
   a-1) Human liver cancer cell line, HepG2; and
   a-2) Normal human liver cell line, Chang.

b. The fermented sword bean solution used in the experiment for test purpose is obtained by dissolving freeze-dried powder of fermented sword beans prepared in the method of the present invention with phosphoric acid buffer solution to prepare a stock solution of 100 mg/ml in concentration; and c. Adequate amount of test cells are implanted into 12 well plates and cultured under the conditions of 5% $Co_2$ and 37° C. for 12 hours. Thereafter, the test cells in the 12 well plates are treated with the fermented sword bean solution prepared in the above paragraph (b) but in different concentrations. The test cells are then cultured in the well plates for another 96 hours.

Thereafter, the test cells are measured for their viability through MTT assay.

Figure 1:
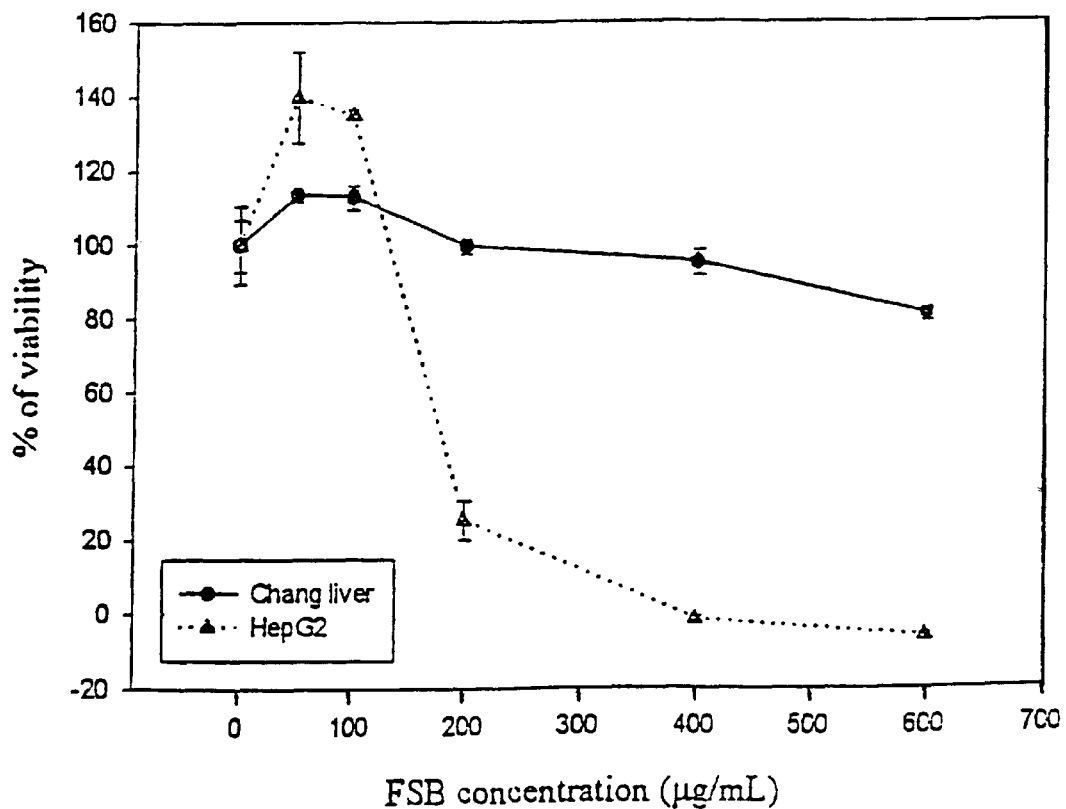
FIG. 1 is a graph showing the effect of fermented sword bean on HepG2 and Chang liver cell lines at normal temperature.
Figure 2:
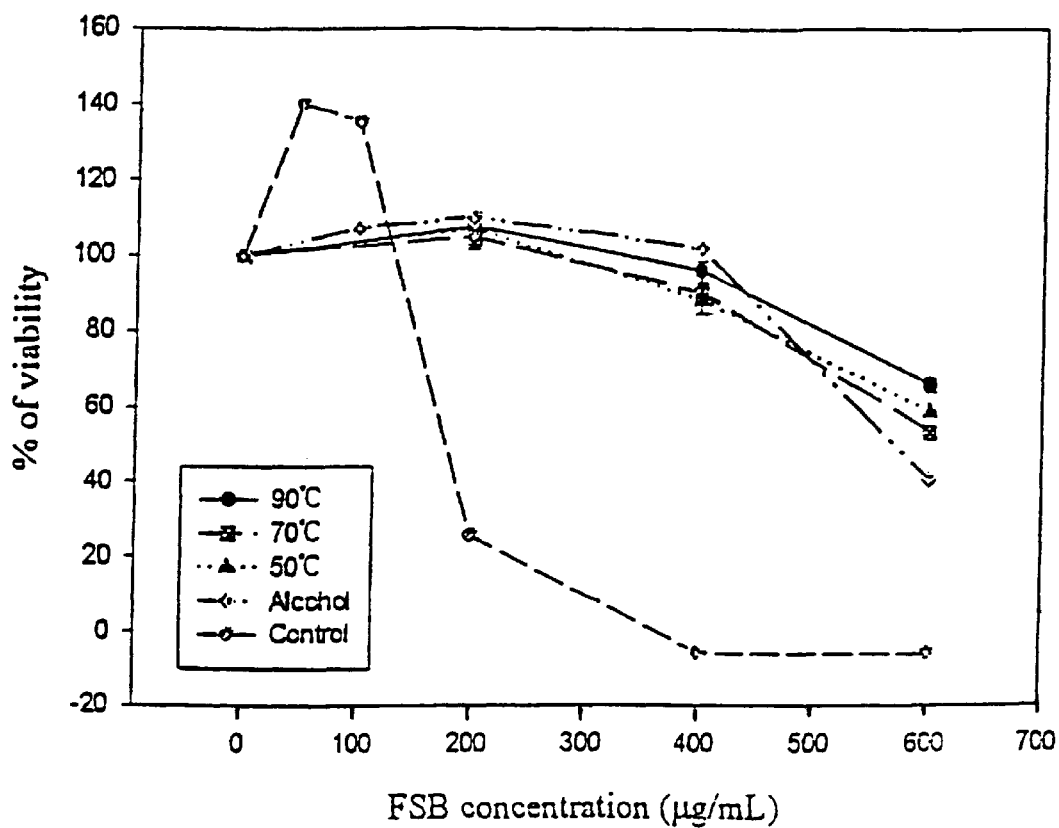
FIG. 2 is a graph showing the effect of temperature and alcohol extraction on the anti-hepatoma activity of the fermented sword bean prepared in the method of the present invention.

The results from the above experiment are indicated in FIGS. 1 and 2.

As can be clearly seen from FIG. 1, after the cultured test cells in the plates are added and treated with fermented sword bean solution of different concentrations and cultured under the conditions of 5% $Co_2$ and 37° C. for another 96 hours, HepG2 cell line treated with fermented sword bean solution of 200 μg/ml in concentration is found to have a cell viability largely dropped by 80%. And, when the HepG2 cell line is treated with fermented sword bean solution of 400μg/ml in concentration, the cell viability thereof would decrease to zero. However, when the fermented sword bean solution of the same concentrations are added to treat the normal Chang liver cell line under the same conditions and for the same period of time, only about 10% of the Chang liver cell line is affected. The results indicate that the fermented sword bean solution will exclusively kill only the cancer cells while it does not significantly affect the normal cells.

FIG. 2 shows the effect of temperature and alcohol extraction on the anti-hepatoma activity of the fermented sword bean solution prepared according to the method of the present invention. When the fermented sword bean solution produced in the method of the present invention is treated with either increased temperature or alcohol extraction, its inhibition action on the HepG2 cell line is apparently reduced. These experiment results suggest that the effective anti-cancer composition of the fermented sword bean solution might be some kind of protein or big-molecule peptide.

From the above description, it proves the fermented sword bean solution produced in the method of the present invention indeed has inhibition action on the liver cancer cells, and the fermented sword bean solution of the present invention has very minor influence on the normal cells while it kills the cancer cells. The effective composition of the fermented sword bean solution might be protein or a big-molecule peptide chain. When comparing to the conventional method of producing raw sword bean troches, the method of the present invention for producing fermented sword beans does not need a series of protein purification processes to obtain the effective ingredient of Concanavalin A contained in the sword bean, nor does the method of the present invention need to proceed below 0° C. in order to maintain the activity of protein in the sword bean. The method of the present invention therefore enables mass production of fermented sword beans at normal temperature and at reduced cost. Moreover, the whole process of the method takes only 80 hours. Therefore, the method of the present invention is improved and more practical and economical than the conventional method.

Following three translated documents are attached to the Specification of the present invention as references:

Ref. No. 1: A Brief Description of Appearance and Functions of *Aspergillus oryzae*;

Ref. No. 2: Examples of Different Forms of *Aspergillus oryzae*; and

Ref. No. 3: An Exemplary Method of Extraction and Separation.

What is claimed is:

1. A method of producing fermented sword beans, comprising following steps:
   a. Disinfecting selected and screened sword beans soaked in water;
   b. Mixing the disinfected sword beans with an adequate amount of *Aspergillus oryzae* added into the sword beans;
   c. Allowing the mixture of disinfected sword beans and *Aspergillus oryzae* to ferment in three separated stages;
   d. Adding an adequate amount of water into the fermented sword beans obtained in step (c) and evenly mixing them;
   e. Extracting and separating the mixture of step (d) to obtain clear solution thereof; and
   f. Freeze-drying the clear solution obtain in step (e) into powder ready for administration.

2. A method of producing fermented sword beans as claimed in claim 1, wherein the disinfecting step (a) is proceeded under a high pressure and at a temperature about 105° C. for one hour, and the disinfected sword beans are allowed to cool to a temperature of 38° C.

3. A method of producing fermented sword beans as claimed in claim 1, wherein the three separated fermentation stages in step (c) includes a first stage of fermentation proceeded at a temperature of 35° C. and a relative humidity between 95% and 100% for 24 hours, a second stage of fermentation proceeded at a temperature between 35° C. and 38° C. and a relative humidity between 85% and 90% for another 24 hours, and a third stage of fermentation proceeded at a temperature between 30° C. and 33° C. and a relative humidity between 70% and 80% for another 32 hours.

4. A method of producing fermented sword beans as claimed in claim 1, wherein the adequate amount of water added into the fermented sword beans in step (d) is about five times in volume of the mixture of the fermented sword beans and the *Aspergillus oryzae* obtained in step (c).

* * * * *